United States Patent
Daneshi Kohan et al.

(10) Patent No.: US 9,872,616 B2
(45) Date of Patent: Jan. 23, 2018

(54) PUPILLARY RESPONSE AND EYE ANTERIOR ASSESSMENT

(71) Applicants: Ehsan Daneshi Kohan, New Westminster (CA); Yaser Mohammadian Roshan, Vancouver (CA); Amirhossein Vejdani, Mashahd (IR); Farzad Hamidi, Vancouver (CA)

(72) Inventors: Ehsan Daneshi Kohan, New Westminster (CA); Yaser Mohammadian Roshan, Vancouver (CA); Amirhossein Vejdani, Mashahd (IR); Farzad Hamidi, Vancouver (CA)

(*) Notice: Subject to any disclaimer, the term of this patent is extended or adjusted under 35 U.S.C. 154(b) by 0 days.

(21) Appl. No.: 15/369,813

(22) Filed: Dec. 5, 2016

(65) Prior Publication Data

US 2017/0079527 A1    Mar. 23, 2017

Related U.S. Application Data

(60) Provisional application No. 62/262,581, filed on Dec. 3, 2015.

(51) Int. Cl.
*A61B 3/14* (2006.01)
*A61B 3/11* (2006.01)
*A61B 3/00* (2006.01)

(52) U.S. Cl.
CPC ............ *A61B 3/112* (2013.01); *A61B 3/0025* (2013.01); *A61B 3/0033* (2013.01); *A61B 3/14* (2013.01)

(58) Field of Classification Search
CPC ..... A61B 3/112; A61B 3/0033; A61B 3/0025; A61B 3/14

USPC ........................................ 351/206, 205, 200
See application file for complete search history.

(56) References Cited

U.S. PATENT DOCUMENTS

| | | | |
|---|---|---|---|
| 7,854,511 B2 | 12/2010 | Molnar et al. | |
| 7,874,675 B2 | 1/2011 | Kandel et al. | |
| 8,454,161 B2 | 6/2013 | Su et al. | |
| 8,550,626 B2* | 10/2013 | Griggio | A61B 3/1025 351/206 |
| 8,820,931 B2 | 9/2014 | Walsh et al. | |
| 9,314,155 B2 | 4/2016 | Verdooner | |
| 2012/0008091 A1 | 1/2012 | Stewart | |

(Continued)

OTHER PUBLICATIONS

Liza M. Cohen, A Novel Computerized Portable Pupillometer Detects and Quantifies Relative Afferent Pupillary Defects, Current Eye Research, Feb. 5, 2015, vol. 40, Issue 11, pp. 1120-1127.

(Continued)

*Primary Examiner* — Tuyen Tra
(74) *Attorney, Agent, or Firm* — NovoTechIP International PLLC

(57) ABSTRACT

Disclosed herein is a pupillary response scanning device and methods for use in performing swinging flashlight test, brightness saturation test, color discrimination test, and color blindness test. The device may include: a housing configured to provide a first isolated eye enclosure for a first eye and a second isolated eye enclosure for a second eye of a patient; one or more visible light sources, one or more infrared light sources, one or more imaging devices in each isolated eye enclosure; and a control system that may be configured for manipulating the visible light sources, infrared light sources and the imaging devices.

7 Claims, 8 Drawing Sheets

(56) References Cited

U.S. PATENT DOCUMENTS

2013/0114042 A1    5/2013  Goldstein et al.
2015/0272438 A1*  10/2015  Yao ..................... A61B 3/102
                                                        351/206

OTHER PUBLICATIONS

Hedenir M. Pinheiro, Development of an effective method and a portable device to evaluate the pupillary reflex, 2015 IEEE 28th International Symposium on Computer-Based Medical Systems.

Nicholas J. Volpe, Portable Pupillography of the Swinging Flashlight Test to Detect Afferent Pupillary Defects, Ophthalmology, Mar. 1999, vol. 107, Issue 10, pp. 1913-1921.

Lada Kalaboukhova, An objective method for measuring relative afferent pupillary defect in glaucomatous optic neuropathy—stimulus optimization, Neuro-ophthalmology, Nov. 2005, vol. 30, Issue 1, pp. 7-15.

Omar Abdeladl, Development of a Portable Near Infrared Camera for Early Detection of Diabetic Ulcers, 2016 32nd Southern Biomedical Engineering Conference (SBEC). IEEE, 2016.

Mei-Lan Ko, Design and analysis of wearable pupillometer for autonomic neuropathy of diabetic patients, Applied optics, Jul. 2014vol. 53, Issue 29, pp. H27-H34.

* cited by examiner

PUPILLARY RESPONSE AND EYE ANTERIOR ASSESSMENT

CROSS REFERENCE TO RELATED APPLICATION

This application claims the benefit of priority from U.S. Provisional Patent Application Ser. No. 62/262,581, filed on Dec. 3, 2015, and entitled "Apparatus, methods and systems for portable optic neuritis, color blindness, and eye abnormalities assessment and quantification," which is incorporated herein by reference in its entirety.

TECHNICAL FIELD

The present application generally relates to the field of ophthalmology, and more particularly to systems and methods for ocular assessment.

BACKGROUND

Relative Afferent Pupillary Defect (hereinafter "RAPD") also known as Marcus-Gunn pupil, is a condition in which pupils respond differently to light stimuli shone in one eye at a time due to unilateral or asymmetrical disease of the retina or optic nerve. Swinging flashlight test or Marcus Gunn test is one of the most basic eye exams that may be used for evaluating RAPD.

Swinging flashlight test may be performed in a dimly-lit room, using a strong light source. Pupillary reactions are observed as the light shines in one eye. Normally, when either eye is exposed to direct light, both eyes will constrict. In an individual with RAPD, shining light into an unaffected eye will cause both pupils to constrict, while shining light into the affected eye will yield a diminished constrictive response in both eyes. There may be drawbacks associated with this test. The major drawback may be the subjectivity of the examiner's opinion about the variations of pupil size and speed of response to light, which are important parameters in evaluating the state of RAPD. Also, the unsymmetrical test situation for either eye, may make the test procedure unreliable for mild RAPDs. Although the response of each eye to light stimuli should be measured independently and in isolation, the ability of swinging flashlight test in providing this condition is limited because both patient's eyes should be open to let the examiner check each pupil size change. Moreover, the ambient light in the room may affect the amount of light received by each eye, which may make the results prone to error.

Brightness Saturation Test (hereinafter "BST") may be used along with swinging flashlight test to quantify RAPD. This method involves placing a series of neutral density filters in front of the intact eye to change the light intensity, and to repeat the swinging flashlight test. More particularly, this method is performed by increasing the density of the filters in front of the intact eye until the constriction of the defective eye is observed to be the same level as its impaired direct reflex.

Color Discrimination Test (hereinafter "CDT") may be used along with swinging flashlight test and BST to quantify RAPD. This method involves placing a red object in front of one eye and asking the patient to choose the most similar color to the object from the color bar in front of the other eye. The amount of discrepancy among the two reds, results in quantification of RAPD. Similarly, due to the subjective and verbal communication between patient and doctor, determination of exact amount of difference between perceived values of the red object by each eye may not be quite possible.

A significant percentage of the human population is affected by Color Blindness. A patient suffering from color blindness may be unable or with limited ability to see color, or distinguish between colors under normal lighting conditions. Screening and more detailed quantitative tests may be developed to detect a color vision deficiency and determine the type and severity of color blindness.

Ishihara color vision test may be considered the most widely used color blindness test. In this test, the patient should be in a room with normal daylight. The examiner asks the patient to find and read a random number in a page which is covered with many dots of various colors, brightness and sizes. The complete test may involve checking 38 different images each on a separate page. Unlike people with normal vision, color blind patients are not able to find a number at all or they see a different number. Although it is one of the most common color blindness detection tests, however, it cannot be used for checking the vision of young children, because they cannot recognize different numbers and correct communication with them may not always be possible.

Farnsworth-Munsell 100 Hue Test is another popular test which makes quantification of color blindness possible. A patient should sort 400 small colored disks in a special order and the results will be compared to the standard known set. The difference between patient's results and the standard set determines the amount of color blindness. Other than the long time needed to perform this test which makes patients tired, the ambient light may affect the patient's perception of colors and may make the results prone to errors.

Problems such as human errors in measuring pupil size using naked eye; variations in testing conditions, such as changes in ambient light; uncontrollable and unintentional changes in penlight intensity due the variations in battery charges and etc., result in a long sought but unfulfilled need in the art for systems and methods that automatically assess and quantify ophthalmologic biomarkers of Marcus-Gunn and color blindness.

Moreover, after performing certain eye surgeries, patients may need to be monitored regularly with short intervals. Limited access to ophthalmologist due to busy appointments may impose a challenge on getting the high standard health service that patients deserve. Also, patients who live in remote areas have very limited access to specialists and cannot be routinely checked up.

Accordingly, there is a need in the art for a system and method that enables the patients to test their eyes at home and share the test results with their doctors, via for example an online method. This may speed up the time that doctors need to monitor their patients and check their bio-markers remotely and it may also increase the accuracy of the tests. There is further a need in the art for systems and methods that provide digital archiving of the test results, which let the doctors track the progression of patients' diseases or treatments over time.

SUMMARY

In one general aspect, a pupillary response scanning device and methods for use thereof in performing swinging flashlight test, brightness saturation test, color discrimination test, and color blindness test is described. The pupillary response scanning device may include: a housing configured to provide a first isolated eye enclosure for a first eye and a second isolated eye enclosure for a second eye of a patient; one or more visible light sources, one or more infrared light sources, one or more imaging devices in each isolated eye enclosure; and a control system that may be configured for manipulating the visible light sources, infrared light sources and the imaging devices. The housing may be configured to keep the eyes isolated from environment and one another to prevent light emitted from sources other than those inside an eye enclosure from entering the eye enclosed in that eye enclosure.

In another general aspect, a method is described for ocular assessment that may include steps of: providing a pupillary response scanning device that may include: a housing configured to provide a first isolated eye enclosure for a first eye and a second isolated eye enclosure for a second eye of a patient; one or more visible light sources, one or more infrared light sources, one or more imaging devices in each isolated eye enclosure; and a control system that may be configured for manipulating the visible light sources, infrared light sources and the imaging devices; continuously illuminating the first and second eyes of the patient with infrared light from the one or more infrared light sources during testing; capturing at least one reference image of the first and the second eye with the one or more imaging devices; illuminating the first eye of the patient with visible light from the one or more visible light sources in the first eye enclosure for a predetermined duration; concurrently capturing at least one first test image of the first and the second eyes with the one or more imaging devices; subjecting the first and the second eyes to a dark adaptation period under infrared illumination from the one or more infrared light sources; illuminating the second eye of the patient with visible light from one or more visible light sources in the second eye enclosure for a predetermined duration; concurrently capturing at least one second test image of the first and the second eyes with the one or more imaging devices; and transmitting the reference images, the first and the second test images to the control system, wherein the control system is configured to process the transmitted images to identify an affected eye and a healthy eye.

According to some implementations, the method for ocular assessment may further include the steps of: illuminating the affected eye with visible white light from one or more visible light sources for a predetermined duration; concurrently capturing at least one first test image of the affected eye with the one or more imaging devices; subjecting the affected eye and the healthy eye to a dark adaptation period under infrared illumination from the one or more infrared light sources; illuminating the healthy eye with visible white light from the one or more visible light sources for a predetermined duration with a predetermined initial intensity; gradually changing the intensity of the visible white light illuminated into the healthy eye; concurrently capturing consecutive test images of the affected eye for each light intensity with the one or more imaging devices; transmitting the first test image and the consecutive test images to the control system. According to one implementation, the control system may be configured to: determine a pupil size for the affected eye in direct white light application from the first test image; determine a pupil size for the affected eye in consensual white light application for each light intensity from the consecutive test images; and find a light intensity at which the pupil size of the affected eye in direct white light application is equal to pupil size for the affected eye in consensual white light application.

According to other implementations, the method for ocular assessment may further include the steps of: illuminating the affected eye with visible red light from one or more visible light sources for a predetermined duration; concurrently capturing at least one first test image of the affected eye with the one or more imaging devices; subjecting the affected eye and the healthy eye to a dark adaptation period under infrared illumination from the one or more infrared light sources; illuminating the healthy eye with visible red light from the one or more visible light sources for a predetermined duration with a predetermined initial intensity; gradually changing the intensity of the visible red light illuminated into the healthy eye; concurrently capturing consecutive test images of the affected eye for each light intensity with the one or more imaging devices; transmitting the first test image and the consecutive test images to the control system. According to one implementation, the control system may be configured to: determine a pupil size for the affected eye in direct red light application from the first test image; determine a pupil size for the affected eye in consensual red light application for each light intensity from the consecutive test images; and find a light intensity at which the pupil size of the affected eye in direct red light application is equal to pupil size for the affected eye in consensual red light application.

In another general aspect, a method for color blindness test is described that may include the steps of: providing a pupillary response scanning device that may include: a housing configured to provide a first isolated eye enclosure for a first eye and a second isolated eye enclosure for a second eye of a patient; one or more visible light sources, one or more infrared light sources, one or more imaging devices in each isolated eye enclosure; and a control system that may be configured for manipulating the visible light sources, infrared light sources and the imaging devices; continuously illuminating the first and second eyes of the patient with infrared light from the one or more infrared light sources during testing; capturing at least one reference image of the first and the second eye with the one or more imaging devices; illuminating the healthy eye with visible light from the one or more visible light sources for a predetermined duration with a predetermined initial wavelength; gradually changing the wavelength of the visible light from an initial wavelength to a final wavelength; concurrently capturing consecutive test images of the first and the second eyes for each wavelength with the one or more imaging devices; and transmitting the first test image and the consecutive test images to the control system. The control system may be configured to determine a pupillary reactivity for the first eye or the second eye to direct light application for each wavelength.

In some applications, the pupillary response scanning device may further include a first adjustment knob and a second adjustment knob. The first adjustment knob may be configured for changing the intensity and/or the wavelength of the one or more visible light sources in the first isolated eye enclosure. The second adjustment knob may be configured for changing the intensity and/or the wavelength of the one or more visible light sources in the second isolated eye enclosure.

DETAILED DESCRIPTION

Disclosed systems and methods directed to assessing ophthalmologic biomarkers for assessment of afferent eye defects and color blindness may include a pupillary response scanning device. The pupillary response scanning device may include: a housing that may provide two isolated eye enclosures for each eye of a patient; at least one imaging device in each eye enclosure that may be configured to capture images of each eye; at least one infrared light source in each eye enclosure that may be configured for illuminating each eye during each test; and at least one visible light source in each eye enclosure that may be configured for emitting visible light of variable intensities and frequencies and may be utilized to provide visible light stimuli for each eye.

The pupillary response scanning device may include a control system that may operate the scanning device to perform different ocular testing procedures described herein (e.g., swinging flashlight test, BST, CDT, and CBT) by exposing each eye of a patient to different light stimuli by manipulating light intensities and frequencies of the visible light sources (i.e., dimming visible light sources, turning the light sources on and off, changing visible light wavelength, etc.) in each eye enclosure and concurrently acquiring image data corresponding to pupillary responses of each eye.

Disclosed systems and methods may utilize a combination of light sources, sensors, imaging devices, and control algorithms for carrying out assessments of the images captured from eyes of the patient to let a doctor diagnose, compare, and follow up Marcus-Gunn pupil, color blindness, and other eye abnormalities.

Figure 1:
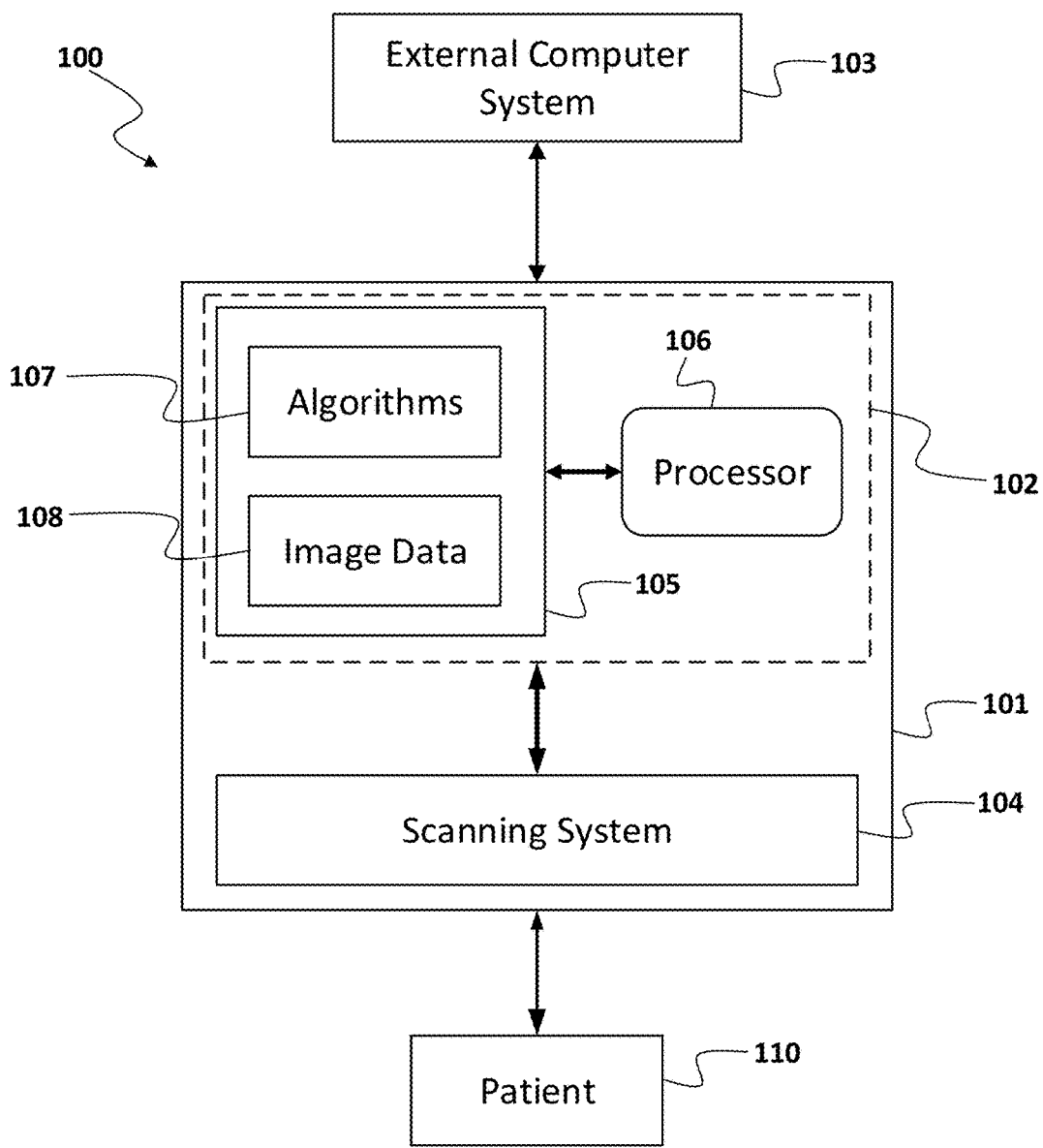
FIG. 1 is a schematic functional block diagram of an example pupillary response evaluation system, according to one or more aspects of the present disclosure.

FIG. 1 is a schematic functional block diagram of an exemplary pupillary response evaluation system 100, according to one or more aspects of the present disclosure. The pupillary response evaluation system 100 is directed to assessing ophthalmologic biomarkers for assessment of afferent eye defects and color blindness according to one or more aspects of this disclosure. Pupillary response evaluation system 100 may include: a pupillary scanning device 101, and a control system 102 that may optionally be embedded in the pupillary scanning device 101. The pupillary scanning device 101 may include a scanning system 104 that may be configured to expose eyes of a patient 110 to various light stimuli and concurrently capture images of the eyes in order to record pupillary responses of both eyes as will be described in more detail later in this disclosure. The recorded pupillary responses by the scanning system 104 may be sent as image data via a communication pathway to the control system 102. The control system 102 may include a memory 105 and a processor 106. The memory 105 may include one or more algorithms 107 and the image data 108 received from the scanning system 104. The algorithms 107 may include, but are not limited to executable instructions for performing different ocular assessment procedures (e.g., swinging flashlight test, BST, CDT, and color blindness test, etc.) and evaluation algorithms (e.g., image processing algorithms, etc.) for evaluating the image data 108 obtained from the ocular assessment procedures. The algorithms 107, when executed by the processor 106, may either cause the control system 102 to operate the scanning system 104 for performing different ocular assessment procedures, and/or may cause the control system 102 to evaluate the image data 108 obtained from different ocular assessment procedures for automatically formulating a diagnosis or helping a doctor to formulate a diagnosis, as will be described in more detail later in this disclosure.

In an aspect, the pupillary response evaluation system 100 may further include an external computer system 103 that may be operatively connected to the pupillary scanning device 101 and may be configured for allowing a user (i.e., doctor) to monitor the evaluation results produced by the control system 102 and formulate a diagnosis. In an implementation, the external computer system 103 may be operatively connected to the pupillary scanning device 101 using an online connection, for example a secured cloud platform. According to other implementations, the external computer system 103 may be operatively connected to the pupillary scanning device 101 using a physical connection, a local network or the like.

In another implementation (not shown in FIG. 1), the control system 102 may be embedded within the external computer system 103 and it may be operatively connected to the pupillary scanning device 101.

Figure 2A:
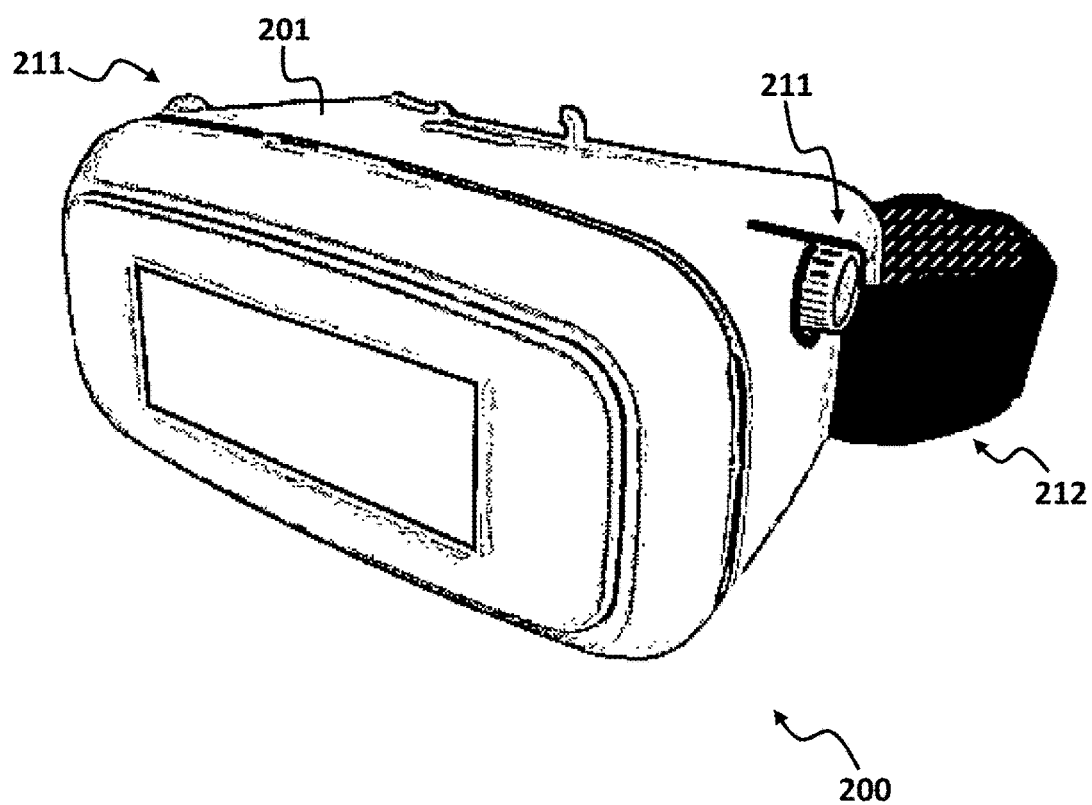
FIG. 2A illustrates a perspective view of a pupillary response scanning device, according to one implementation of the present disclosure.
Figure 2B:
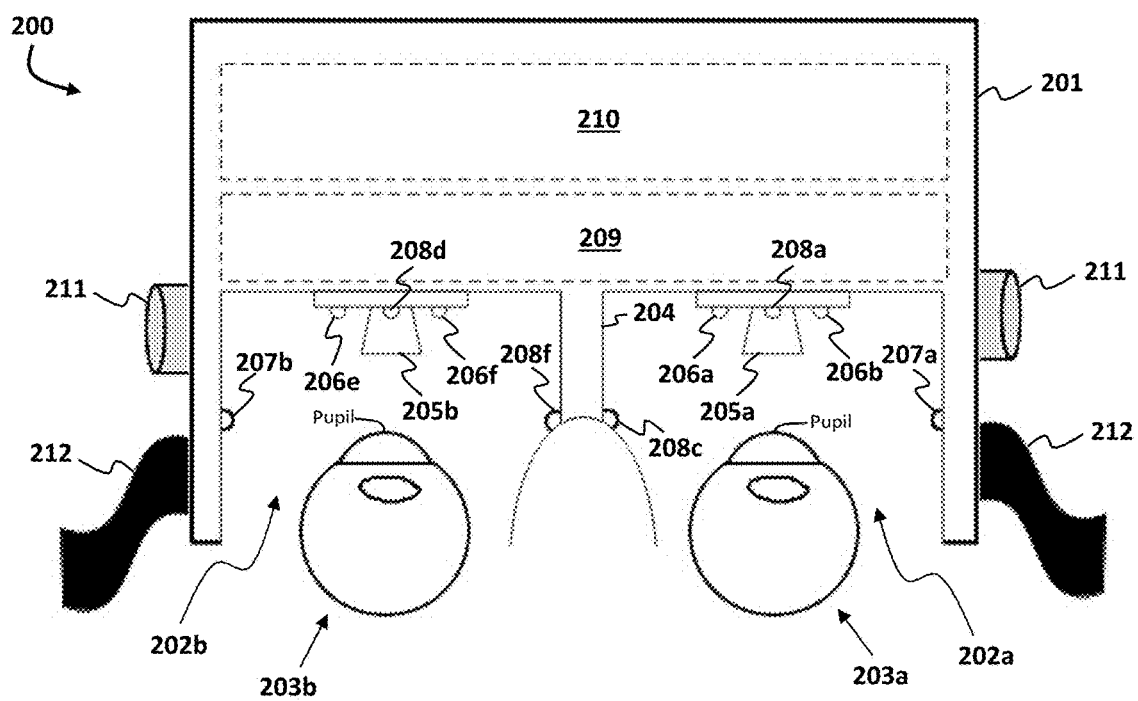
FIG. 2B illustrates a top view of the pupillary response scanning device shown in FIG. 2A.
Figure 2C:
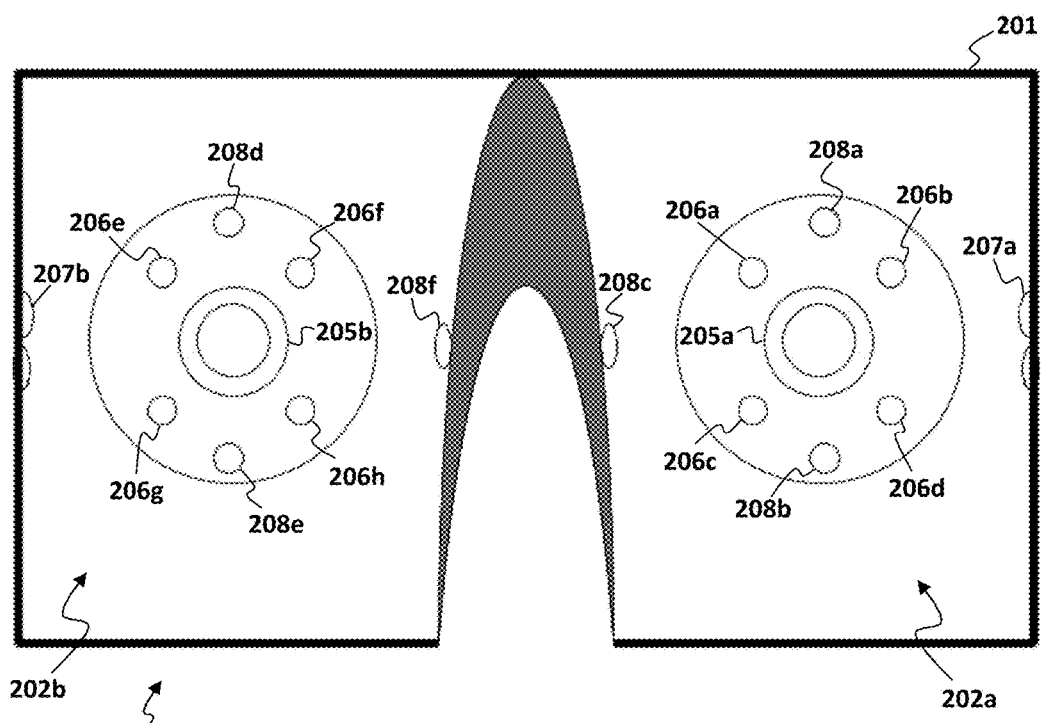
FIG. 2C illustrates a front view of the pupillary response scanning device shown in FIG. 2A.

FIG. 2A illustrates a perspective view of a pupillary response scanning device 200, according to one implementation of the present disclosure. The pupillary response scanning device 200 may correspond to the pupillary scanning device 101. FIG. 2B illustrates a top view of a pupillary response scanning device 200 shown in FIG. 2A. FIG. 2C illustrates a front view of a pupillary response scanning device 200 shown in FIG. 2A.

Referring to FIGS. 2A-2C, the pupillary response scanning device 200 may include a housing 201 that may provide two isolated eye enclosures 202a and 202b for eyes 203a-b of a test subject (i.e., patient) such that each eye may be kept isolated from the other eye and the environment. In an aspect, the housing 201 may be fixed in front of a patient's eyes such that eye enclosures 202a and 202b may be pressed against the patient's eye orbitals to prevent light emitted from sources other than the device 200 itself from entering the intended subject's eyes. Eye enclosures 202a and 202b may be separated and isolated from one another by a separator 204, such that each eye 203a or 203b may be kept in full isolation from the other eye, i.e., no light may be sensed by a contralateral eye when light sources are emitting light to either eyes.

At least two imaging devices (e.g., cameras) 205a and 205b may be included within eye enclosures 202a and 202b. Imaging devices 205a and 205b may be configured for capturing images of the eyes 203a-b of the patient during the eye assessment procedures. According to some implementations, each eye enclosure may include at least one imaging device.

With continuing reference to FIGS. 2B and 2C, pupillary response scanning device 200 may include a number of infrared light sources 206a-h. The infrared light sources 206*a-h* may include for example infrared light emitting diodes (IR-LEDs) capable of emitting infrared light. Infrared light sources 206*a-h* may be arranged on the periphery of imaging devices 205*a-b* and directed towards the eyes 203*a-b*. According to some implementations, at least one infrared light source may be positioned in each eye enclosure that may be directed towards the eye enclosed in that enclosure. Light beams emitted from each infrared light source may shine in each eye and reflect back towards each imaging device. According to an implementation, there may be infrared light sources dedicated to each eye, for example, infrared light sources 206*a-d* may be dedicated to eye 203*a* and infrared light sources 206*e-h* may be dedicated to eye 203*b*.

In an aspect, each eye enclosure 202*a* (202*b*) may include at least one visible light source 207*a* (207*b*), such as a light-emitting diode (LED) that may be configured for streaming a wide range of visible light. According to some implementations, visible light source 207*a* (207*b*) may produce visible light of various intensities and wavelengths. For example, visible light source 207*a* (207*b*) may be a wide-spectrum LED capable of streaming a wide range of visible light. According to other implementations, visible light source 207*a* (207*b*) may be a number of colored light sources, such as colored LEDs, each streaming a color (e.g., white, red, etc.). In an implementation, visible light sources 207*a*, 207*b* may be placed in each eye enclosure 102*a*, 102*b* on the side of each eye 103*a* (103*b*), such that the light rays emitted from each visible light source 207*a* (207*b*) may be parallel to the surface of each eye 103*a* (103*b*).

According to some implementations, each eye enclosure 202*a* (202*b*) may include at least one light sensor that may be configured for sensing intensity and frequency of light at each moment inside each eye enclosure 202*a* (202*b*). Light sensors 208*a-f* may be placed in front of each eye 203*a* (203*b*) on the periphery of each imaging device 205*a* (205*b*) and at either sides of each eye 203*a* (203*b*). Sensors 208*a-f* may be configured for converting the amount of light intensity and wavelength in each eye enclosure 202*a* (202*b*) to electrical signals. The electrical signals may be utilized in a light intensity control mechanism that may be configured to control and adjust the intensity and frequency of light that is generated by each visible light source 207*a* (207*b*). According to some implementations, a known algorithm, for example, pulse width modulation (PWM) may be utilized for controlling the intensity, wavelength, and frequency of the light generated by visible light sources 207*a-b*.

Referring to FIG. 2B, the pupillary response scanning device 200 may further include a control system 209 and a power unit 210. The control system 209 may be configured to provide an example implementation of the FIG. 1 control system 102.

In an aspect, the control system 209 may be configured to manipulate the infrared light sources 206*a-h* and the visible light sources 207*a-b*. As used herein, in one implementation, manipulating means turning the infrared light sources 206*a-h* and the visible light sources 207*a-b* on and off and changing the intensity and wavelength of the visible light sources 207*a-b* based on the executable instructions stored in the memory of the control system 209. Moreover, the control system 209 may be configured to manipulate the imaging devices 205*a* and 205*b* by causing the imaging devices 205*a* and 205*b* to capture the images of eyes 203*a-b* based on the executable instructions stored in the memory of the control system 209.

In some implementations, control system 209 may be operatively coupled to light sensors 208*a-f*, for purposes that may include, but are not limited to calculating the desired intensity and frequency of the light that may need to be generated by each visible light source 207*a* (207*b*) inside each eye enclosure 202*a* (202*b*). The electrical signals sent by light sensors 208*a-f* may be fed back to a control algorithm stored on memory 105 (labeled in FIG. 1) to modify the parameters that are being used to generate PWM signals to control the intensity, wavelength, and frequency of the light generated by visible light sources 207*a-b*.

According to an implementation, power unit 210 may be included in pupillary response scanning device 200 and it may include optional batteries or in another implementation the power may be provided from an external source via a wired connection.

With further reference to FIGS. 2A-2C, according to an implementation, the pupillary response scanning device 200 may be designed with a portable goggle-shaped configuration that may be strapped around the eyes of the subject. Consequently, the pupillary response scanning device 200 may further include an adjustable strap 212.

Referring to FIGS. 2A and 2B, according to some implementations, the pupillary response scanning device 200 may further include adjustment knobs 211 that may be configured for manually adjusting the light intensity of visible light sources 107*a* and 107*b* in each eye enclosure 102*a* (102*b*), independently. In an aspect, the pupillary response scanning device 200 may be configured for evaluating the reactivity of pupil in each eye 203*a* or 203*b* to both direct and consensual light application. As used herein, in one example, direct light application means scanning the pupillary response in the same eye to which light stimulus is being applied by the visible light source 207*a* or 207*b*. Consensual light application may mean scanning the pupillary response in the eye opposite to that which is receiving light stimulus from the visible light source 207*a* or 207*b*.

Example 1: Swinging Flashlight Test

Figure 3A:
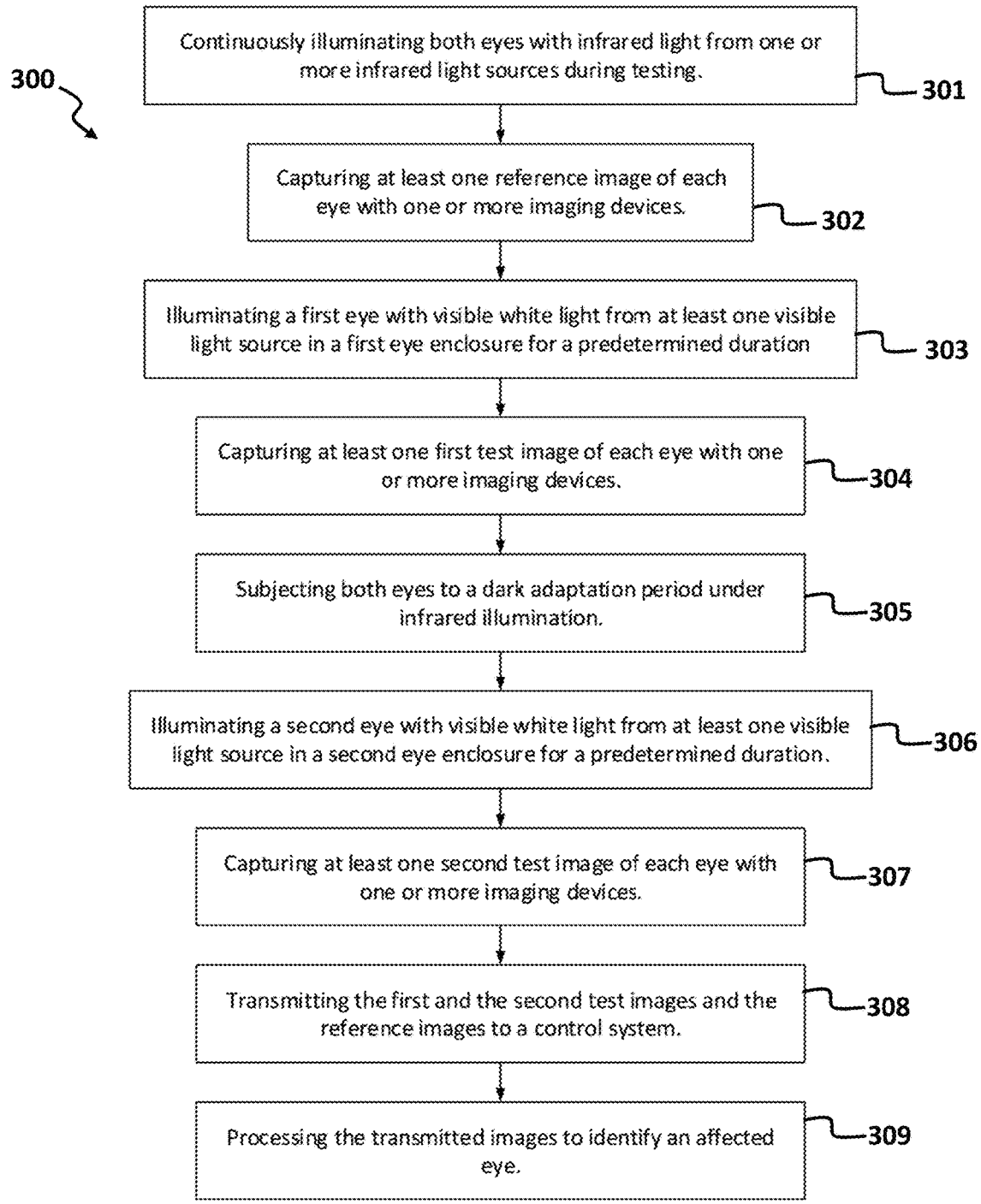
FIG. 3A illustrates an exemplary process for performing a swinging flashlight test using the pupillary response scanning device shown in FIG. 2A.

In an aspect, the pupillary response scanning device 200 may be configured for performing a swinging flashlight test. FIG. 3A illustrates an exemplary process 300 for performing a swinging flashlight test using the pupillary response scanning device 200 shown in FIG. 2A. Operations in the process 300 may include: continuously illuminating both eyes with infrared light from one or more infrared light sources during testing (step 301); capturing at least one reference image of each eye with one or more imaging devices (step 302); illuminating a first eye with visible white light from at least one visible light source in a first eye enclosure for a predetermined duration (step 303); capturing at least one first test image of each eye with one or more imaging devices (step 304); subjecting both eyes to a dark adaptation period under infrared illumination (step 305); illuminating a second eye with visible white light from at least one visible light source in a second eye enclosure for a predetermined duration (step 306); capturing at least one second test image of each eye with one or more imaging devices (step 307); transmitting the first and the second test images and the reference images to a control system (step 308); and processing the transmitted images to identify an affected eye (step 309).

Referring to FIGS. 1 and 3A, operations in the process 300 may be stored on the memory 105 as executable instructions that once executed by the processor 106 may allow the control system 102 to operate the pupillary response scanning device 200 to perform a swinging flashlight test.

As an illustration, referring to FIGS. 2B, 2C, and 3A, example operations of the process 300 may be performed by the pupillary response scanning device 200 as follows. Referring to 301, infrared light sources 206a-d in eye enclosure 202a and infrared light sources 206e-h in eye enclosure 202b may be turned on in order to continuously illuminate eyes 203a-b. Moving on to 302, at least one reference image of eye 203a may be captured with imaging device 205a and at least one reference image of eye 203b may be captured with imaging device 205b. I Moving on to 303, visible light source 207a in eye enclosure 202a may be turned on in order to illuminate eye 203a with visible white light for an arbitrary and predetermined duration. In some implementations, the predetermined duration may be for example 2 to 3 seconds. Referring to 304, at this point at least one first test image of eyes 203a-b may be captured with imaging devices 205a-b. After that, referring to 305, visible light source 207a in eye enclosure 202a may be turned off in order to subject both eyes 203a-b to a dark adaptation period under infrared illumination from infrared light sources 206a-d for a predetermined duration. In some implementations, the dark adaptation period may be a period of 5 seconds.

Moving on to 306, visible light source 207b in eye enclosure 202b may be turned on in order to illuminate eye 203b with visible white light for a predetermined duration. Referring to 307, at this point at least one second test image of eyes 203a-b may be captured with imaging devices 205a-b.

With continuing reference to FIGS. 2B, 2C, and 3A, moving on to 308, the reference images captured in 302, the first test images captured in 304, and the second test images captured in 307 may be transmitted to the control system 209. Moving on to 309, referring to FIG. 1, the transmitted images may be stored on the memory 105 as the image data 108. The processor 106 may execute an image processing algorithm that may be stored as executable instructions on the memory 105 to cause the control system 102 to perform operations in order to identify an affected eye. Such operations, may include for example, processing the image data 108 to determine pupillary response measurements, such as pupil reaction/redilation latency, pupil reaction duration, pupil reaction rate, maximal pupil area change, percentage of maximal pupil area change, rebound percentage during redilation. The pupillary response measurements may be carried out by calculating the size of the patient's pupils based on the transmitted images, calculating the amount of constriction in each pupil under both direct and consensual light application by comparing the first and the second test images to the reference images. Accordingly, by comparing the pupillary response of the eye 203a to pupillary response of the eye 203b in the image data, the eye with a diminished pupillary response may be identified as the affected or the abnormal eye.

Example 2: Brightness Saturation Test (BST)

Figure 3B:
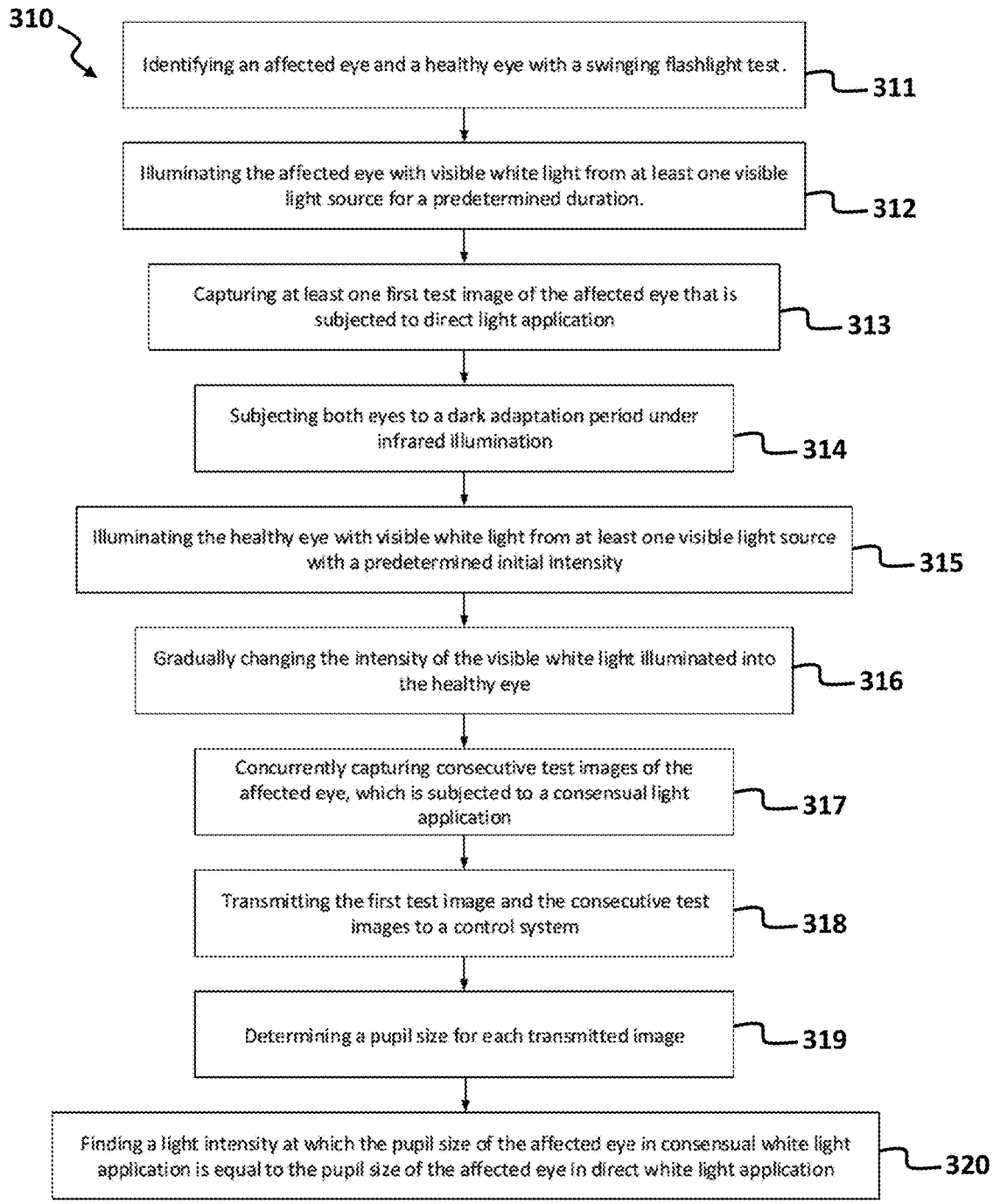
FIG. 3B illustrates an exemplary process for performing a brightness saturation test (BST) using the pupillary response scanning device shown in FIG. 2A.

In an aspect, the pupillary response scanning device 200 may be configured for performing a BST. FIG. 3B illustrates an exemplary process 310 for performing BST using a pupillary response scanning device 200 shown in FIG. 2A. Operations in the process 310 may include: identifying an affected eye and a healthy eye with a swinging flashlight test (step 311) that may be performed by exemplary operations of the process 300 of FIG. 3A; illuminating the affected eye with visible white light from at least one visible light source for a predetermined duration (step 312); capturing at least one first test image of the affected eye that is subjected to direct light application (step 313); subjecting both eyes to a dark adaptation period under infrared illumination (step 314); illuminating the healthy eye with visible white light from at least one visible light source with a predetermined initial intensity (step 315); gradually changing the intensity of the visible white light illuminated into the healthy eye (step 316); concurrently capturing consecutive test images of the affected eye, which is subjected to a consensual light application (step 317); transmitting the first test image and the consecutive test images to a control system (step 318); determining a pupil size for each transmitted image (step 319); and finding a light intensity at which the pupil size of the affected eye in consensual white light application is equal to the pupil size of the affected eye in direct white light application (step 320).

Referring to FIGS. 1 and 3B, operations in the process 310 may be stored on the memory 105 as executable instructions that once executed by the processor 106 may allow the control system 102 to operate the pupillary response scanning device 200 to perform a BST. As an illustration, referring to FIGS. 2B, 2C, and 3B, example operations of the process 310 may be performed by the pupillary response scanning device 200 as follows. Referring to 311, the affected eye and the healthy eye may be identified by a swinging flashlight test performed by the pupillary response scanning device 200 with a flow of operations as was described in detail in connection with example 1. In this example, eye 203a may be considered to be, for example, the affected eye. Moving on to 312, visible light source 207a in eye enclosure 202a may be turned on in order to illuminate the affected eye 203a with visible white light for an arbitrary and predetermined duration. Referring to 313, at this point at least one first test image of the affected eye 203a may be captured with imaging device 205a. After that, referring to 314, visible light source 207a in eye enclosure 202a may be turned off in order to subject both eyes 203a-b to a dark adaptation period under infrared illumination from infrared light sources 206a-d. Moving on to 315, visible light source 207b in eye enclosure 202b may be turned on in order to illuminate the healthy eye 203b with visible white light with a predetermined initial white light intensity.

Referring to 316, the intensity of the visible white light may be gradually changed by the control system 209 that may receive feedback from light sensors 208a-f. In an implementation, visible white light with a maximum light intensity may be illuminated into the healthy eye 203b and then the light intensity may be reduced from this maximum initial value to lower intensities in a stepwise manner. Alternatively, visible white light with a minimum light intensity may be illuminated into the healthy eye 203b and then the light intensity may be increased from this minimum initial value to higher intensities in a stepwise manner. Referring to 317, concurrently consecutive test images may be captured with imaging device 205a from the affected eye 203a while the light intensity of the light source 207b is being gradually changed in the eye enclosure 202b.

Moving on to 318, the first test image and the consecutive test images may be transferred to the control system 209. Referring to FIG. 1, the transmitted images may be stored on the memory 105 as the image data 108. The processor 106 may execute an algorithm that may be stored as executable instructions on the memory 105 to cause the control system 102 to perform operations in order to find a light intensity at which the pupil size of the affected eye 203a in consensual white light application that may be measured by processing is equal to the pupil size of the affected eye 203a in direct white light application. Such operations may include: measuring the pupil size of the affected eye 203a by processing the first test images captured from the affected eye 203a under a direct light application; measuring a pupil size of the affected eye 203a for each consecutive image captured from the affected eye 203a under a consensual light application with different light intensities; and comparing the measured pupil sizes to find a light intensity at which the pupil size of the affected eye 203a in consensual white light application is equal to the pupil size of the affected eye 203a in direct white light application. In an aspect, the difference between the intensities of the direct white light application and the intensity of the consensual light application for which the pupil size of the affected eye 203a is equal to that of the affected eye 203a under direct light application may be utilized by pupillary response scanning device 200 to automatically formulate a quantitative diagnosis or alternatively referring to FIG. 1, the results produced by device 101 may be transmitted to the external computer system 103 and a doctor at the external computer system 103 may utilize the results to formulate a quantitative diagnosis.

Example 3: Color Discrimination Test (CDT)

Figure 3C:
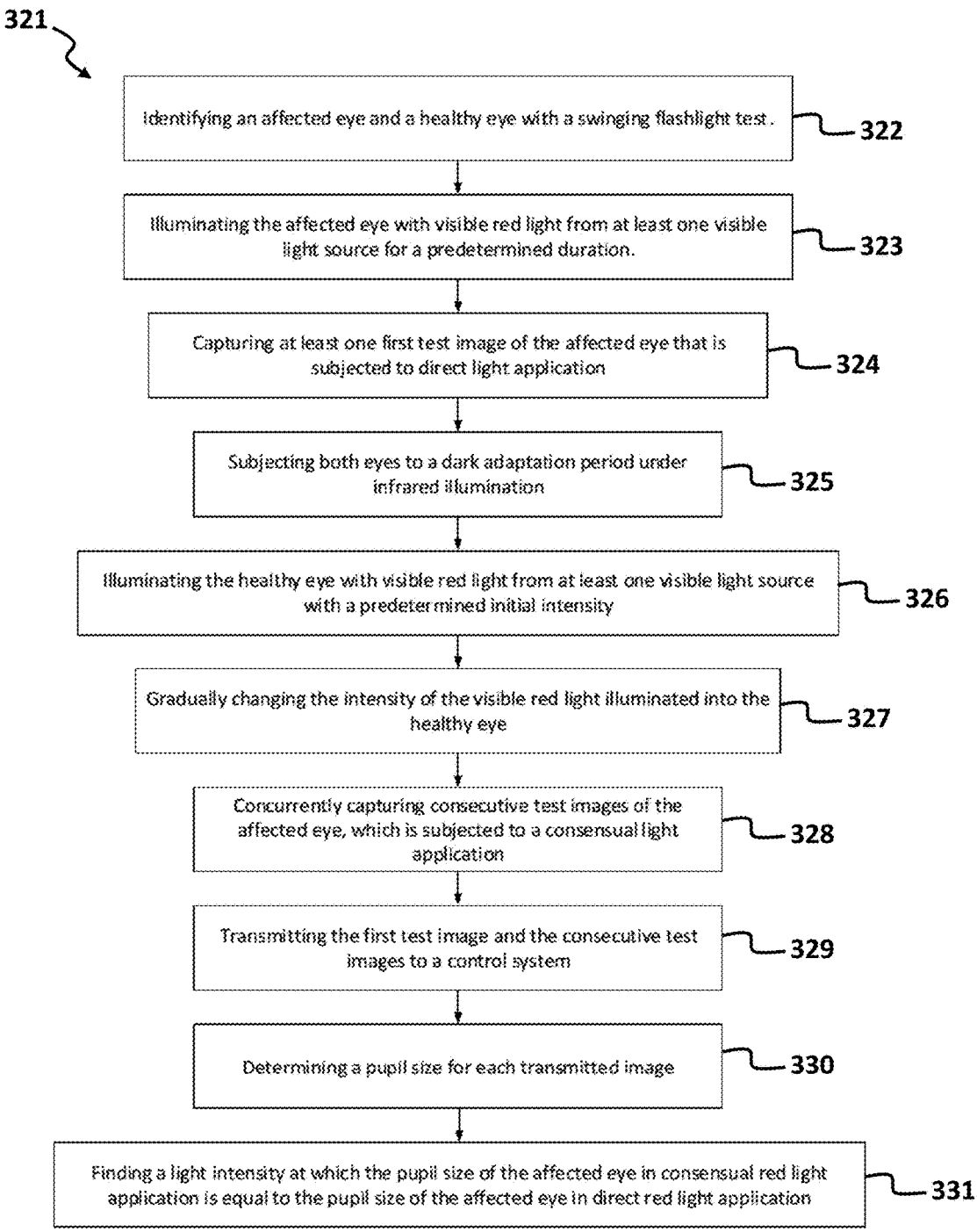
FIG. 3C illustrates an exemplary process for performing a color discrimination test (CDT) using the pupillary response scanning device shown in FIG. 2A.

In an aspect, the pupillary response scanning device 200 may be configured for performing a CDT. FIG. 3C illustrates an exemplary process 321 for performing a CDT using the pupillary response scanning device 200 shown in FIG. 2A. Operations in the process 321 may include: identifying an affected eye and a healthy eye with a swinging flashlight test (step 322) that may be performed by exemplary operations of the process 300 of FIG. 3A; illuminating the affected eye with visible red light from at least one visible light source for a predetermined duration (step 323); capturing at least one first test image of the affected eye that is subjected to direct light application (step 324); subjecting both eyes to a dark adaptation period under infrared illumination (step 325); illuminating the healthy eye with visible red light from at least one visible light source with a predetermined initial intensity (step 326); gradually changing the intensity of the visible red light illuminated into the healthy eye (step 327); concurrently capturing consecutive test images of the affected eye, which is subjected to a consensual red light application (step 328); transmitting the first test image and the consecutive test images to a control system (step 329); determining a pupil size for each transmitted image (step 330); and finding a red light intensity at which the pupil size of the affected eye in consensual red light application is equal to the pupil size of the affected eye in direct red light application (step 331).

Referring to FIGS. 1 and 3C, operations in the process 321 may be stored on the memory 105 as executable instructions that once executed by the processor 106 may allow the control system 102 to operate the pupillary response scanning device 200 to perform a CDT.

As an illustration, referring to FIGS. 2B, 2C, and 3C, example operations of the process 321 may be performed by the pupillary response scanning device 200 as follows. Referring to process 322, the affected eye and the healthy eye may be identified by a swinging flashlight test performed by the pupillary response scanning device 200 with a flow of operations as was described in detail in connection with example 1. In this example, eye 203a may be considered to be, for example, the affected eye. Moving on to 323, visible light source 207a in eye enclosure 202a may be turned on in order to illuminate the affected eye 203a with visible red light for an arbitrary and predetermined duration. Referring to 324, at this point at least one first test image of the affected eye 203a may be captured with imaging device 205a. After that, referring to 325, visible light source 207a in eye enclosure 202a may be turned off in order to subject both eyes 203a-b to a dark adaptation period under infrared illumination from infrared light sources 206a-d. Moving on to 326, visible light source 207b in eye enclosure 202b may be turned on in order to illuminate the healthy eye 203b with visible red light with a predetermined initial red light intensity. Referring to 327, the intensity of the visible red light may be gradually changed by the control system 209 that may receive feedback from light sensors 208a-f. In an implementation, visible red light with a maximum light intensity may be illuminated into the healthy eye 203b and then the light intensity may be reduced from this maximum initial value to lower intensities in a stepwise manner, alternatively, visible red light with a minimum light intensity may be illuminated into the healthy eye 203b and then the light intensity may be increased from this minimum initial value to higher intensities in a stepwise manner. Referring to 328, concurrently consecutive test images may be captured with imaging device 205a from the affected eye 203a while the light intensity of the light source 207b is being gradually decreased in the eye enclosure 202b.

Moving on to 329, the first test image and the consecutive test images may be transferred to the control system 209. Referring to FIG. 1, the transmitted images may be stored on the memory 105 as the image data 108. The processor 106 may execute an algorithm that may be stored as executable instructions on the memory 105 to cause the control system 102 to perform operations in order to find a red light intensity at which the pupil size of the affected eye 203a in consensual red light application is equal to the pupil size of the affected eye 203a in direct red light application. Such operations may include: measuring the pupil size of the affected eye 203a by processing the first test images captured from the affected eye 203a under a direct red light application; measuring a pupil size of the affected eye 203a for each consecutive image captured from the affected eye 203a under a consensual red light application with different light intensities; and comparing the measured pupil sizes to find a red light intensity at which the pupil size of the affected eye 203a in consensual red light application is equal to the pupil size of the affected eye 203a in direct red light application. In an aspect, the difference between the intensities of the direct red light application and the intensity of the consensual red light application for which the pupil size of the affected eye 203a is equal to that of the affected eye under direct red light application may be utilized by pupillary response scanning device 200 to automatically formulate a quantitative diagnosis or alternatively referring to FIG. 1, the results produced by device 101 may be transmitted to the external computer system 103 and a doctor at the external computer system 103 may utilize the results to formulate a quantitative diagnosis.

Example 4: Color Blindness Test

Figure 3D:
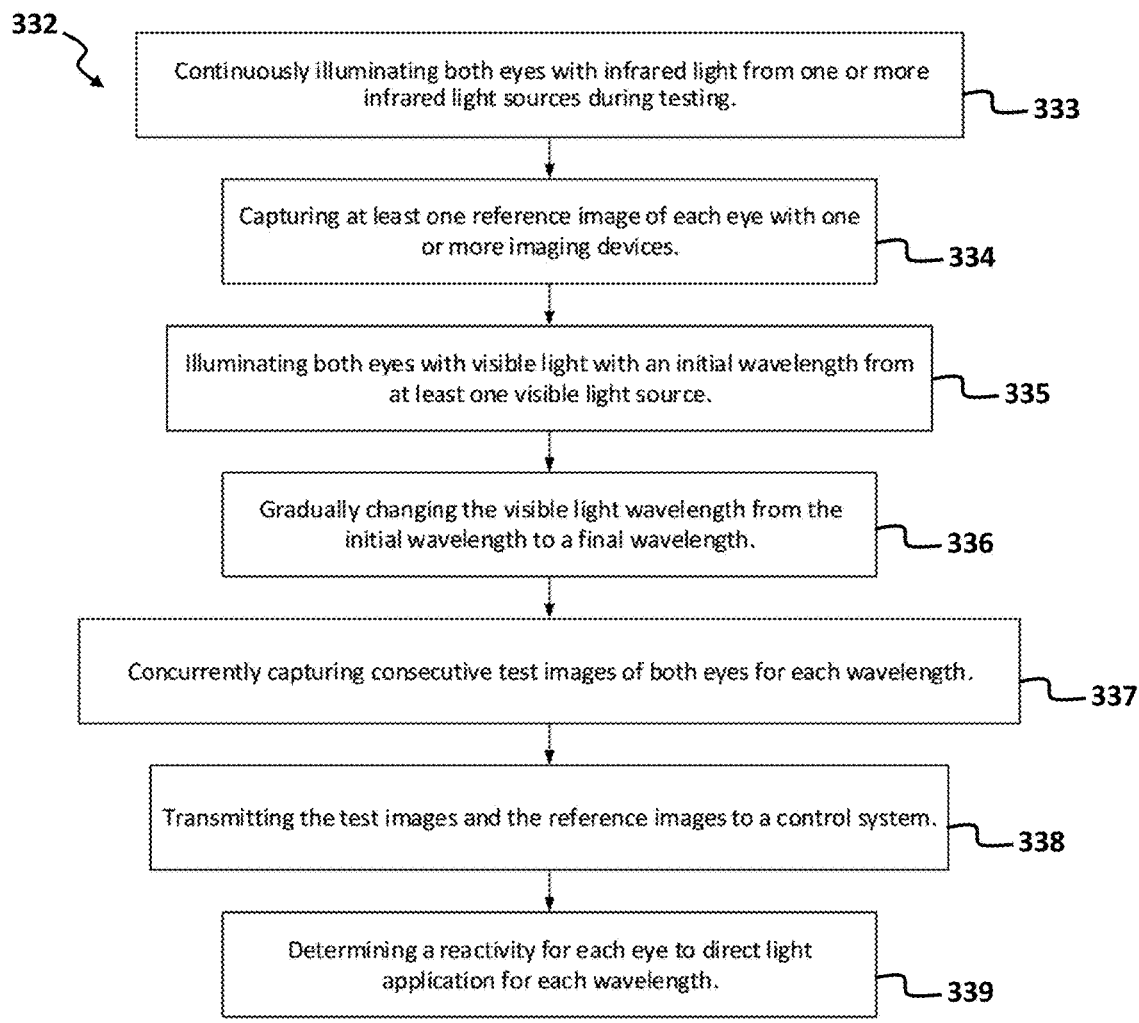
FIG. 3D illustrates an exemplary process for performing a color blindness test using a pupillary response scanning device shown in FIG. 2A.

In an aspect, pupillary response scanning device 200 may be configured for performing a color blindness test. FIG. 3D illustrates an exemplary process 332 for performing a color blindness test using the pupillary response scanning device 200 shown in FIG. 2A. Operations in the process 332 may include: continuously illuminating both eyes with infrared light from one or more infrared light sources during testing (step 333); capturing at least one reference image of each eye with one or more imaging devices (step 334); illuminating both eyes with visible light with an initial wavelength from at least one visible light source (step 335); gradually changing the visible light wavelength from the initial wavelength to a final wavelength (step 336); concurrently capturing consecutive test images of both eyes for each wavelength (step 337); transmitting the test images and the reference images to a control system (step 338); determining a reactivity for each eye to direct light application for each wavelength (step 339); and determining the sensitivity of each eye to different visible light wavelengths based on the determined reactivity for each eye (step 340).

Referring to FIGS. 1 and 3D, operations in the process 332 may be stored on the memory 105 as executable instructions that once executed by the processor 106 may allow the control system 102 to operate the pupillary response scanning device 200 to perform a color blindness test.

As an illustration, referring to FIGS. 2B, 2C, and 3D, example operations of the process 332 may be performed by the pupillary response scanning device 200 as follows. Referring to 333, infrared light sources 206a-d in eye enclosure 202a and infrared light sources 206e-h in eye enclosure 202b may be turned on in order to continuously illuminate eyes 203a-b. Moving on to 334, at least one reference image of eye 203a may be captured with imaging device 205a and at least one reference image of eye 203b may be captured with imaging device 205b. Moving on to 335, visible light sources 207a-b in eye enclosures 202a-b may be turned on in order to illuminate both eyes 203a-b with visible light with a predetermined initial wavelength. Referring to 336, the wavelength of the visible light may be gradually changed by the control system 209 that may receive feedback from light sensors 208a-f In an implementation, visible light with a maximum wavelength may be illuminated into both eyes 203a-b and then the wavelength may be reduced from this maximum initial value to lower wavelengths in a stepwise manner, alternatively, visible light with a minimum wavelength may be illuminated into both eyes 203a-b and then the wavelength may be increased from this minimum initial value to higher wavelengths in a stepwise manner. Referring to 337, concurrently consecutive test images may be captured with imaging devices 205a-b from both eyes 203a-b while the wavelength of the light sources 207a-b are being gradually changed in the eye enclosures 202a-b.

Moving on to 338, the reference images captured in 334, and the consecutive test images captured in 337 for each wavelength may be transmitted to the control system 209. Moving on to 339, referring to FIG. 1 the transmitted images may be stored on the memory 105 as the image data 108. The processor 106 may execute an image processing algorithm that may be stored as executable instructions on the memory 105 to cause the control system 102 to perform operations in order to carry out pupillary response measurements, such as determining the reactivity of each eye to direct light application for each wavelength. Based on the reactivity of each eye to direct visible light application with different wavelengths, the sensitivity of each eye to different visible light wavelengths that corresponds to different visible light colors may be determined. In an aspect, the device 101 may formulate a diagnosis automatically based on the obtained results or alternatively the device 101 may only report the reactivity of each eye to each color stimulus and a user (i.e., doctor) at the external computer system 103 may use the reports transmitted by the device 100 to formulate a diagnosis.

Referring to FIGS. 2A-2C, in an aspect, the BST and CDT procedures may be performed manually utilizing the pupillary response scanning device 200 of the present disclosure. The light intensities in the BST and CDT procedures may be changed using adjustment knobs 211 manually by the patient or an operator and instead of using an algorithm to automatically finding a light intensity for which the pupil size of the affected eye in consensual white or red light applications is equal to the pupil size of the affected eye in direct white or red light applications, the operator may ask the patient to change the intensity using the adjustment knobs 211 and find the right intensity based on their judgment, i.e., patient's perceived intensities of consensual white or red light applications becomes the same as patient's perceived intensities of direct white or red light applications.

Example 5: Eye Abnormality Detection Test

In an aspect, the pupillary response scanning device 200 may be configured for performing eye abnormality detection tests. To this end, images may be captured from the whole surface of each eye including pupil, iris, and sclera. The captured images may then be sent to a control system that may employ an image processing algorithm to process the captured images for detecting, analyzing, and tracking any abnormalities in short and long term. The abnormalities may include, but are not limited to, nevus in the iris, inflammation in the iris (i.e., hypopyon), blood in the iris (i.e., hyphemia), surgery marks, and the size, number, and pattern of blood vessels on sclera.

Referring to FIGS. 1, 2B, and 2C, as an illustration, example operations of eye abnormality detection test may be performed by the pupillary response scanning device 200 as follows: imaging devices 205a-b may capture images of the entire surface of eyes 203a-b. The captured images may then be transmitted to the control system 102 to be stored on the memory 105 as the image data 108. The memory 105 may include image processing algorithms that once executed by the processor 106, may cause the control system 102 to detect abnormalities in eyes 203a-b. The control system 102 may be configured to store the test results of a patient in the memory 105 for future references and it may be configured to track the abnormalities in eyes of a patient based on the recorded test results on the memory 105.

According to some implementations, the predetermined duration for visible light stimulation of each eye may be 2 to 3 seconds. In other implementations, the dark adaptation period may be a period of for example 5 seconds.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," and any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

The Abstract of the Disclosure is provided to allow the reader to quickly identify nature of disclosed subject matter. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that any claim requires more features than the claim expressly recites. Rather, as the following claims reflect, inventive subject matter lies in less than all features of a single disclosed example. Thus the following claims are hereby incorporated into the Detailed Description, with each claim standing on its own as a separately claimed subject matter.

What is claimed is:

1. A method for ocular assessment comprising:
   providing a pupillary response scanning device including:
      a housing configured to provide a first isolated eye enclosure for a first eye and a second isolated eye enclosure for a second eye of a patient;
      a visible light source in the first isolated eye enclosure and the second isolated eye enclosure;
      an infrared light source in the first isolated eye enclosure and the second isolated eye enclosure;
      an imaging device in the first isolated eye enclosure and the second isolated eye enclosure; and
      a control system configured to manipulate the visible light source, the infrared light source and the imaging device;
   continuously illuminating the first and second eyes of the patient with infrared light from the infrared light source during a test;
   capturing a reference image of the first and the second eye with the imaging device during the test;
   illuminating the first eye of the patient with visible light from the visible light source in the first eye enclosure for a predetermined duration;
   concurrently with illuminating first eye of the patient with the visible light, capturing a first test image of the first and the second eyes with the imaging device;
   subsequent to capturing the first test image, subjecting the first and the second eyes to a dark adaptation period under infrared illumination from the infrared light source;
   illuminating the second eye of the patient with visible light from the visible light source in the second eye enclosure for a predetermined duration;
   concurrently with illuminating the second eye of the patient with the visible light, capturing a second test image of the first and the second eyes with the imaging device; and
   transmitting the reference image and the first and the second test images to the control system; and
   processing via the control system the transmitted reference image and the first and second test images to identify an affected eye and a healthy eye;
   wherein, the housing is configured to keep the first and second eyes isolated from environment and one another to prevent light emitted from sources other than the visible light source and the infrared light source placed in each of the first and second eye enclosures from entering the first and second eyes enclosed in the first and second eye enclosures.

2. The method according to claim 1, further comprising:
   illuminating the affected eye with visible white light from the visible light sources for a predetermined duration;
   concurrently with illuminating the affected eye with the visible white light, capturing at a third test image of the affected eye with the imaging device;
   subsequent to capturing the third test image, subjecting the affected eye and the healthy eye to a dark adaptation period under infrared illumination from the infrared light source;
   illuminating the healthy eye with visible white light from the visible light source for a predetermined duration with a predetermined initial intensity;
   gradually changing the intensity of the visible white light illuminated into the healthy eye;
   during gradually changing the intensity of the visible while light, concurrently capturing consecutive test images of the affected eye for each light intensity with the imaging device;
   transmitting the third test image and the consecutive test images to the control system;
   determining via the control system a pupil size for the affected eye in direct white light application from the third test image;
   determining via the control system a pupil size for the affected eye in consensual white light application from the consecutive test images; and
   identifying a light intensity at which the pupil size of the affected eye in direct white light application is equal to pupil size for the affected eye in consensual white light application.

3. The method according to claim 2, wherein:
   the pupillary response scanning device further comprises a first adjustment knob and a second adjustment knob,
   the first adjustment knob is configured for changing the intensity of the visible light source in the first isolated eye enclosure, and
   the second adjustment knob is configured for changing the intensity of the visible light source in the second isolated eye enclosure.

4. The method according to claim 1, further comprising:
illuminating the affected eye with visible red light from the visible light source for a predetermined duration;
concurrently with illuminating the affected eye with visible red light, capturing a third test image of the affected eye with the imaging device;
subsequent to capturing the third test image, subjecting the affected eye and the healthy eye to a dark adaptation period under infrared illumination from the infrared light source;
illuminating the healthy eye with visible red light from the visible light source for a predetermined duration with a predetermined initial intensity;
gradually changing the intensity of the visible red light illuminated into the healthy eye;
during gradual changing the intensity of the visible red light, concurrently capturing consecutive test images of the affected eye for each light intensity with the imaging device;
transmitting the third test image and the consecutive test images to the control system;
determining via the control system a pupil size for the affected eye in direct red light application from the third test image;
determining via the control system a pupil size for the affected eye in consensual red light application for each light intensity from the consecutive test images; and
identifying a light intensity at which the pupil size of the affected eye in direct red light application is equal to the pupil size for the affected eye in consensual red light application.

5. The method according to claim 4, wherein:
the pupillary response scanning device further comprises a first adjustment knob and a second adjustment knob,
the first adjustment knob is configured for changing the intensity of the visible light source in the first isolated eye enclosure, and
the second adjustment knob is configured for changing the intensity of the visible light source in the second isolated eye enclosure.

6. A method for color blindness test, comprising:
providing a pupillary response scanning device including:
a housing configured to provide a first isolated eye enclosure for a first eye and a second isolated eye enclosure for a second eye of a patient;
a visible light source in the first isolated eye enclosure and the second isolated eye enclosure;
an infrared light source in the first isolated eye enclosure and the second isolated eye enclosure;
an imaging device in the first isolated eye enclosure and the second isolated eye enclosure; and
a control system configured to manipulate the visible light source, the infrared light source, and the imaging devices;
continuously illuminating the first and second eyes of the patient with infrared light from the infrared light source during a test;
capturing a reference image of the first and the second eyes with the imaging device during the test;
illuminating a healthy eye selected from among the first and the second eyes with visible light from the visible light source for a predetermined duration with a predetermined initial wavelength;
gradually changing the wavelength of the visible light from an initial wavelength to a final wavelength;
concurrently with gradual changing the wavelength of the visible light capturing consecutive test images of the first and the second eyes for each wavelength with the imaging device;
transmitting the first test image and the consecutive test images to the control system; and
determining via the control system a pupillary reactivity for the first eye or the second eye to direct visible light application for each wavelength,
wherein, the housing is configured to keep the first and second eyes isolated from environment and one another to prevent light emitted from sources other than the visible light source and the infrared light source inside the first and second eye enclosures from entering the first and second eye enclosures and thereby to the first and second eye.

7. The method according to claim 6, wherein:
the pupillary response scanning device further comprises a first adjustment knob and a second adjustment knob,
the first adjustment knob is configured for changing the wavelength of the visible light source in the first isolated eye enclosure, and
the second adjustment knob is configured for changing the wavelength of the visible light source in the second isolated eye enclosure.

* * * * *